United States Patent
Bassot et al.

(10) Patent No.: US 8,408,068 B2
(45) Date of Patent: Apr. 2, 2013

(54) DEVICE FOR TESTING THE COATING OF A VANE BASE

(75) Inventors: Alain Bassot, Bois le Roi (FR); Laurent Dudon, Viry-Chatillon (FR); Anne-Claire Perriau, Vaux le Penil (FR)

(73) Assignee: SNECMA, Paris (FR)

( * ) Notice: Subject to any disclaimer, the term of this patent is extended or adjusted under 35 U.S.C. 154(b) by 303 days.

(21) Appl. No.: 12/919,017

(22) PCT Filed: Feb. 25, 2009

(86) PCT No.: PCT/FR2009/050296
§ 371 (c)(1), (2), (4) Date: Aug. 24, 2010

(87) PCT Pub. No.: WO2009/112757
PCT Pub. Date: Sep. 17, 2009

(65) Prior Publication Data
US 2011/0000308 A1 Jan. 6, 2011

(30) Foreign Application Priority Data
Feb. 25, 2008 (FR) ...................... 08 51183

(51) Int. Cl.
*G01N 3/08* (2006.01)
(52) U.S. Cl. ............................ 73/826; 73/831
(58) Field of Classification Search ............... 73/826, 73/827, 831, 150 A, 760
See application file for complete search history.

(56) References Cited

U.S. PATENT DOCUMENTS

| 3,802,255 | A | | 4/1974 | Struthers et al. |
| 4,541,287 | A | * | 9/1985 | Roper ............................... 73/827 |
| 5,160,243 | A | * | 11/1992 | Herzner et al. ............ 416/220 R |
| 5,240,375 | A | * | 8/1993 | Wayte ........................ 416/219 R |
| 5,601,933 | A | * | 2/1997 | Hajmrle et al. ................ 428/660 |
| 6,250,166 | B1 | * | 6/2001 | Dingwell et al. ................ 73/810 |
| 6,267,558 | B1 | * | 7/2001 | Dingwell et al. ......... 416/219 R |
| 6,910,866 | B2 | | 6/2005 | Bassot et al. |
| 7,108,484 | B2 | | 9/2006 | Thenaisie et al. |
| 7,144,602 | B2 | | 12/2006 | Bengtsson et al. |
| 2005/0252304 | A1 | | 11/2005 | Woodward et al. |
| 2006/0216429 | A1 | | 9/2006 | Bengtsson et al. |
| 2011/0138926 | A1 | * | 6/2011 | Bassot et al. ..................... 73/826 |

FOREIGN PATENT DOCUMENTS

| EP | 1 598 655 | 11/2005 |
| EP | 1 705 261 | 9/2006 |

OTHER PUBLICATIONS

U.S. Appl. No. 12/919,268, filed Aug. 25, 2010, Bassot, et al.

* cited by examiner

*Primary Examiner* — Max Noori
(74) *Attorney, Agent, or Firm* — Oblon, Spivak, McClelland, Maier & Neustadt, L.L.P.

(57) ABSTRACT

A device for testing a coating for a turbomachine rotor disk blade root, including two test piece halves, each including a bearing surface coated with the coating, one counter test piece including two bearing surfaces, and a machine including a first holding system for the counter test piece and a second holding system for holding the test piece halves around the counter test piece. With a tensile mechanism, the holding systems are subjected to predetermined tensile cycles along the tensile axis, during which the tensile force is transmitted from one holding system to the other via the respective bearing surfaces contacting the counter test piece and the test piece halves. The second holding system includes a resilient return mechanism allowing for the two test piece halves to open up in a direction perpendicular to the tensile direction.

11 Claims, 2 Drawing Sheets

DEVICE FOR TESTING THE COATING OF A VANE BASE

This invention relates to the field of antifriction coatings applied to the blade roots of rotary machines, and quality control thereof. More precisely, the invention relates to a device for testing a coating capable of coating a turbomachine rotor blade root. This may be a terrestrial or aeronautical turbomachine, and namely an airplane turbo-reactor or turboprop.

Blades, and in particular fan blades in aeronautical turbomachines are extremely stressed mechanical parts. For this reason the blade root, which is the holding portion of the blade, is a particularly critical portion of the part. The blade root comprises contact surfaces with the rotor disk, or bearing surfaces, which in operation are subjected to pressures and high temperatures. In order to reduce the stresses, and namely the shearing stresses, which are applied to the bearing surfaces of the blade roots, antifriction coatings are used in a known manner. These so-called antifretting coatings can be deposited namely by thermal projection. They may be multi-layered.

As failures at the bearing surfaces of the blade root, e.g. due to the apparition of cracks, are one of the major types of failure in blades, the quality of the antifriction coating is essential. In order to ensure the quality of this coating, and stability of the coating on the interface thereof with the blade itself, micrographic tests are performed in a known manner, which consist in sectioning the coating and the blade root and examining the aspect of this section under the microscope. It is also known to test the quality of the coating through standard hardness tests, tensile or shear adhesion tests, or perform measurements of thickness.

However, it appeared that the various tests prove to be insufficient for distinguishing high quality coatings from just acceptable quality coatings, and for forming a precise opinion about the durability and mechanical aspect in use of the coating deposited on the blade root.

If a cycle for a blade (or a blade root) is to designate the set of stresses to which the latter is subjected during an operating phase (in flight for a turbo-reactor mounted on an airplane), i.e. from start to stop, then the previous statement means that current tests do not allow to establish a difference of quality between the various coatings as long as they withstand a number of cycles in a satisfactory manner.

The aim of the invention is to define a device for testing a coating capable of coating a turbomachine rotor blade root, allowing to perform a more differentiating test than prior tests as to the quality of the coatings tested, and the results of which are highly correlated with the actual assessments of stability in time of the blade root coatings, as found throughout the lifetime of a blade, i.e. commonly from 10,000 to 15,000 cycles.

This aim is achieved in that the device comprises two test piece halves, each having a bearing surface coated with said coating, one counter test piece having two bearing surfaces, and a machine comprising a first holding system for holding the counter test piece along a tensile axis, a second holding system for holding the test piece halves around the counter test piece, and tensile means for subjecting the holding systems to predetermined tensile cycles along the tensile axis, during which tensile strain is transmitted from one holding system to the other via the respective bearing surfaces contacting each other of the counter test piece and the test piece halves; and in that the second holding system comprises resilient return means allowing for the two test piece halves to open up in a direction perpendicular to the tensile direction in response to an opening force applied to these two test piece halves by the counter test piece during a tensile cycle.

The principle of the test thus defined is basically different from previously known tests. Indeed, it consists in subjecting coated test pieces to fatigue tests representing stresses to which the blade roots will be exposed during the lifetime of the blade. Advantageously, the device does not require the use of real blades, but merely the use of test piece halves, each having a bearing surface coated with the coating to be tested. It should be noted that furthermore, it is perfectly possible for each test piece half to have not only one, but several bearing surfaces, the counter test piece then comprising one bearing surface corresponding to each of these bearing surfaces of the two test piece halves.

The first and second holding systems respectively hold the test piece halves and the counter test piece facing each other, so as to match their bearing surfaces. The holding systems are then subjected to tensile motions relatively to each other by known means, so as to subject the bearing surfaces, and namely the bearing surfaces of the test piece halves, to stresses representing those experienced by a blade root in operation.

Such stresses are simulated by tensile cycles during which the counter test piece undergoes strains in the tensile direction. Such strains vary as a function of time according to a predetermined cycle, the so-called tensile cycle. Preferably, for each tensile cycle, tension is increased from an initial zero, or at least low value (with respect to the maximum value) up to the maximum value, then returning to the initial value. The initial value and the maximum value, independently one and/or the other, may be maintained for some time. Of course, other tensile cycle profiles can be envisaged, depending on how the different operating phases of the turbomachine are to be simulated. The run-up rate parameter, i.e. the increase of the tensile force per unit of time, can also be used as a variable capable of optimization.

In a known manner, attaching a blade to a rotor disk is done in general by means of a mortise-and-tenon coupling forming an attachment. This attachment is composed of a tenon made at one radially interior end of the blade, the blade root, which secured in a mortise provided on the periphery of the rotor disk. The blade roots on the one hand, the rotor disk tenons or bosses formed between the rotor disk mortises on the other hand, are thus respectively complementary dovetail shapes, and are arranged radially in the opposite direction so as to ensure mutual fastening between the blades and the rotor disk.

In an impeller, the blades are evenly attached on the outer periphery of the rotor disk, which thus comprises as many fastening cells and dovetail tenons as there are blades to be fastened.

The attachments of the blades to the rotor disk thus form a pattern repeated in the circumferential direction and comprising the dovetail tenon of the rotor disk with the two blade root halves enclosing the same in the impeller. This is the pattern reproduced by the counter test piece enclosed by the two test piece halves.

As already mentioned, in the test machine integrated into the device, the second holding system comprises resilient return means allowing for the two test piece halves to be opened in a direction perpendicular to the tensile direction in response to an opening force applied to these two test piece halves by the counter test piece during a tensile cycle. Indeed, during a tensile cycle, namely if the bearing surfaces of the test piece halves and/or the counter test piece are sloping, the counter test piece will bear on the test piece halves, and may have a tendency to open up the test piece halves in a transverse direction, perpendicular to the tensile direction. For this to be avoided, the second holding system advantageously comprises the above-mentioned resilient return means allowing for the relative positions of the counter test piece and the test piece halves to be maintained, which represent the actual positions of the blade root or a rotor disk tenon in a turbomachine.

According to one embodiment, the bearing surfaces of the test piece halves are sloping with respect to the tensile axis, so as to represent the shape of the bearing surfaces of a turbomachine rotor blade root. Thus, the angle formed by the bearing surface of the test piece halves represents the one formed by a blade root bearing surface in a turbomachine with respect to the radial direction thereof. Advantageously, the angle of the bearing surfaces with respect to the tensile direction can be close to 45°; more generally, this angle may vary between 30 and 60°.

Furthermore, the test piece halves may represent a blade root not only through the shape of their bearing surfaces, but also through their material. Thus, the test piece halves are usually manufactured from the same material as the blade root, typically from a titanium or nickel base alloy.

For the same reasons, it is also possible to choose a material identical to that of the rotor disk for the counter test piece, i.e. also from a titanium or nickel base alloy. This allows for a more faithful representation of the behavior of the blade root with respect to the rotor disk.

According to one embodiment, the bearing surfaces of the counter test piece are sloping with respect to the tensile axis, so as to represent the shape of the bearing surfaces of a turbomachine rotor disk tenon. Thus, the angle formed by the bearing surface of the counter test piece represents the one formed by a rotor disk tenon bearing surface in a turbomachine with respect to the radial direction thereof. Thereby, the stress which the bearing surface of the counter test piece applies to the test piece half represents the one the bearing surface of a rotor disk tenon applies to the bearing surface of the blade root, in a turbomachine. Preferably, the bearing surfaces of the counter test piece are inclined by an angle within 30 and 60°, and in general, an angle close to 45° is chosen.

According to one embodiment, the resilient return means comprise at least one bar of resilient material, deforming while remaining in its range of elastic deformation during tensile cycles. The bar thus has some capability of deformation enabling the machine to represent, simulate, the deformations effectively found in operation in the turbomachine, be it deformations of the blade root and/or of the tenon of the rotor disk. Due to this possibility of the two test piece halves to open up, the representativeness of the results obtained by means of the test device is further increased.

According to a variant of the preceding embodiment, the second holding system comprises two posts parallel to the tensile axis and used for maintaining the two test piece halves, said bar connecting these posts along a direction perpendicular to the tensile axis. The two posts parallel to the tensile axis, close to the test piece halves, allow to make sure that the latter are held in place during tensile cycles. For this purpose, it is preferable for the test piece halves to be relatively elongated, so as to facilitate rotational locking.

Moreover, as the opening strains in a transverse direction to the tensile direction will go through said at least one bar, the latter is easy to size depending on the extension strains it will undergo and the elongation considered admissible under the effect of such strains.

According to a variant of the preceding embodiment, the test device further comprises means for measuring the opening of the test piece halves during the test. Thereby, it is possible at any time to ensure that the relative positions of the counter test piece and the test piece halves really correspond to what was envisaged.

According to one embodiment, the test piece halves have close to the bearing surfaces thereof a shape representing turbomachine rotor blade root halves, and the tensile axis is arranged substantially in the radial direction of the blade root halves. This arrangement allows for the test piece halves to be tested under conditions faithfully reproducing actual operating and stress conditions. Also, the simulation of the behavior of the coating for a blade root is not limited to the specific area of the coating, but incorporates the portion of the blade root located close to the bearing surface(s).

Also, according to one embodiment, the counter test piece has close to the bearing surfaces thereof a shape representing the shape of a turbomachine rotor disk tenon. In this case, the effect of the counter test piece reproducing that of the rotor disk tenon on the blade root is more realistic, as it is capable of reproducing the behavior of the rotor disk tenon, not only immediately adjacent to the bearing surface(s), but also throughout the portion of the tenon located close to the bearing surfaces, i.e. usually the whole end of the tenon-shaped counter test piece.

It should be noted that in the device, more or less faithfully depending on the embodiment chosen, the test piece halves facing each other are comparable with the opposite faces of a blade root, the counter test piece being in turn comparable with the rotor disk tenon used for fastening the blade to the rotor. Thus, while on a turbomachine it is the blade root which is enclosed and secured between two tenons of the rotor disk, in the test machine, it is rather the two test piece halves which enclose a counter test piece on either side, representing a tenon of the rotor disk. It has been found that in spite of this apparently inverted arrangement, excellent representativeness of the results is obtained.

According to one embodiment, the side of the test piece halves located on the side of the counter test pieces has no undercut. Therefore, they are cost-efficient, as they are easy to machine by 3-axis machining. The same is true for the counter test piece. Furthermore, the test piece halves can even have a convex exterior shape on the side of the counter test piece.

Finally, it should further be noted that the displacements of the test pieces in a tensile direction can be measured and recorded by a displacement measuring system, such as a comparator or a gage.

The invention will be better understood and the advantages thereof will be more apparent from reading the following detailed description of embodiments represented by way of example and not being restrictive. The description refers to the appended drawings, in which.

Figure 1:
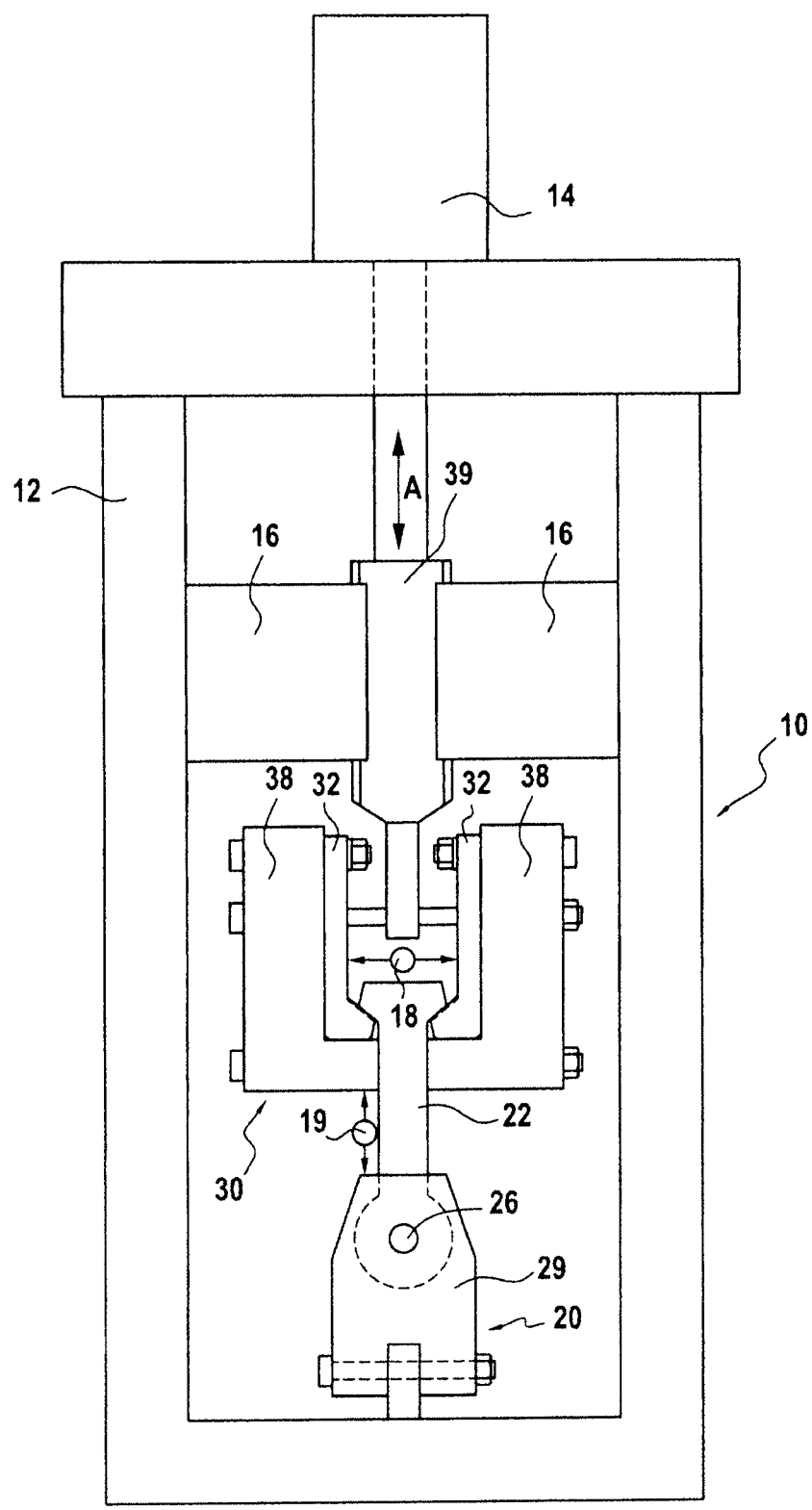
FIG. 1 is an axial sectional view of an inventive test device.

With reference to FIG. 1, we are now going to describe a test device 10 of a coating capable of being applied to a blade root according to the invention. This device 10 comprises a machine comprising first of all a framework 12 generally composed of a mechanically welded frame. This framework 12 supports two holding systems 20 and 30.

The first holding system 20 located in the lower portion of the machine comprises a fixed column 29 holding the counter test piece 22 in place. The counter test piece 22 comprises a bore through which goes a spindle 26 of the first holding system, by means of which the counter test piece 22 is maintained, no matter which tensile stresses it will receive.

The second holding system 30 is used to hold two test piece halves 32 in place. This second holding system 30 comprises a mobile beam 39 set into a straight alternating translatory movement in a vertical direction along the double arrow A, by a linear actuator 14 or any other equivalent actuating means. This beam 39 is guided in its alternating translatory motion by slide bars 16. The holding system 30 further comprises means for rigidly connecting the test piece halves 32 with respect to the beam 39, namely comprising the above-mentioned posts 38.

The characteristics of the linear actuator 14 are chosen so that the latter can impart on the second holding system 30 with respect to the first one 20 translatory motions representing those performed by a blade, and more precisely by the blade root, with respect to the rotor disk during the operation of the turbomachine to which belongs the blade. Such motions are due to significant centrifugal forces received by the blades during rotation of the engine, comparable with radial tension on the blade.

Usually, an attempt is made to reproduce the operating conditions of the blade root, both by the in particular radial strains imposed thereupon and the amplitude of the motions of the blade root. The amplitude of the latter motions depends on the parts interacting with the blade root; therefore, they are highly relevant for the quality of the testing. In the machine presented, such parts are on one side the holding posts 38, and on the other side (the internal side), the counter test piece 22 which is comparable with the tenon of the rotor disk, supposed to hold the blades in a turbomachine. It should be noted, however, that the device can be used for testing the coatings in directions, or with tensile forces, which are different from the usual stress conditions of the blade root and the bearing surfaces thereof.

For the framework 12 and the linear actuator 14 of the inventive machine, standard components usually employed in machines for cyclic tensile testing of mechanical parts can be used. The cycles to be reproduced generally have the following characteristics: A number of cycles which may reach 10,000 or 15,000 cycles; a maximum force applied varying between 15,000 and 30,000 daN.

The counter test piece 22 comprises a bore 24, and the first holding system comprises a spindle 26 by which the counter test piece 22 is held, no matter which tensile stresses it will receive.

Finally, the relative displacements of the test piece halves with respect to the counter test piece are measured and recorded by a measuring system 19.

Figures 2A, 2B:
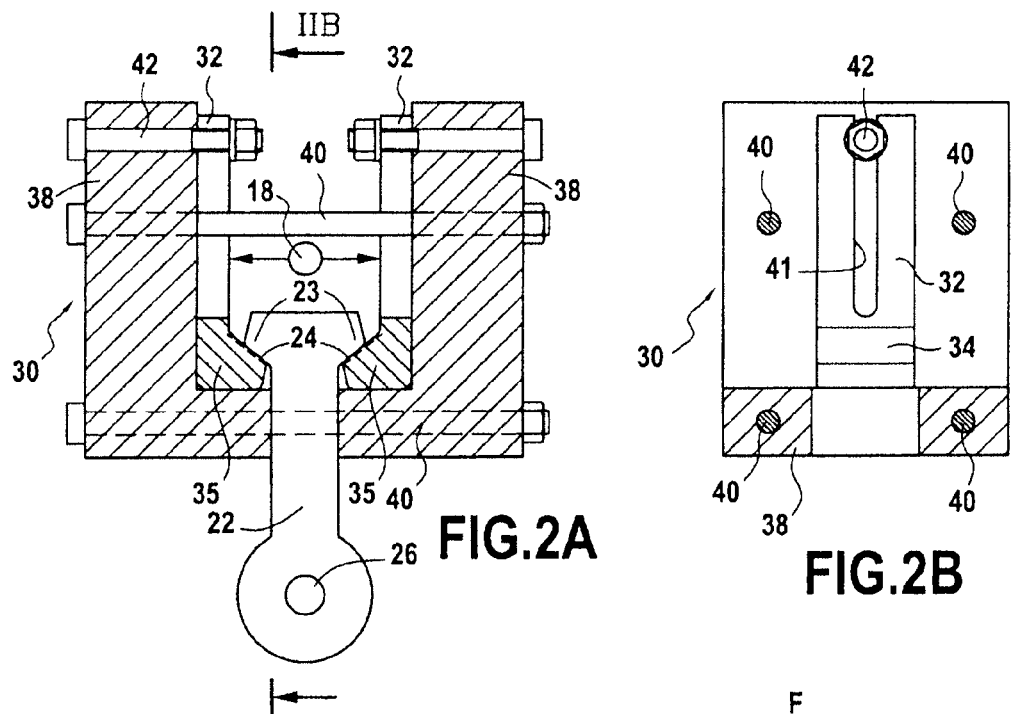
FIGS. 2A and 2B are sectional views of the center portion of this device, respectively front and side views.

With reference to FIGS. 2A and 2B, we are now going to describe the operation of the center portion of the test device according to the invention. FIG. 2A is a sectional view presenting the two test piece halves 32, held on the one hand in the second holding system 30 (posts 38), and on the other hand by the counter test piece 22. The role of the second holding system 30 is to hold the two test piece halves, and more precisely the bearing surfaces 24 thereof, opposite the corresponding bearing surfaces (reference number 25, FIG. 3) of the counter test piece 22, and to transmit to the test piece halves 32 an alternating translatory motion with respect to the counter test piece 22.

The counter test piece 22, at one of the ends thereof (the one at the top in FIG. 1), has a relatively symmetrical bulb, the sides 23 of which project in cantilever fashion on either side of the spindle thereof. The bottom exterior surfaces (as seen in FIG. 1) of these sides 23 are the contact or bearing surfaces of the counter test piece 22. These bearing surfaces reproduce the shape of the rotor disk tenon of the turbomachine on which the blade root is mounted. At the other end thereof, the counter test piece 22 has fastening means, allowing for fastening thereof to the test machine via first means for holding the same, used for holding and fastening the counter test piece during tensile testing. Herein, such holding means comprise a bore 24, provided for a fastening spindle of the test machine to go through.

The bearing surfaces 24 of the test piece halves 32 can be found on the inclined top faces of bulges 35 formed on the base of the test piece halves 32. Such bearing surfaces are contact surfaces comparable with the bearing surfaces of a blade root. When the second holding system undergoes an upward tensile stress (as seen in FIG. 1), the respective bearing surfaces 24 and 25 of the test piece halves and the counter test piece make contact, and thereby resist the upward displacement of the second holding system 30, allowing for the coating 34 deposited on the bearing surfaces 24 of the test piece halves to be tested, put to the test.

While the test piece halves 32 and the counter test piece 22 are used up in the tests, as the test leads to the deformation thereof, the other parts of the machine, on the contrary, are reusable parts.

The second holding system 30 comprises two posts 38 parallel to the tensile axis and used to hold the two test piece halves, each being fastened to one test piece half 32. Fastening can be done namely by means of bolts 42. On the one hand, the bolts 42 go through the post 38 and are moreover fastened through the test piece half 32 in a bore, a slotted hole or an open slotted hole 41, as represented in FIG. 2B.

Even though it is possible for the two posts 38 to be fastened rigidly to each other or even for them to form a single part, it is on the contrary advantageous for them to be independent portions of the second holding system 30.

Herein, two independent portions means that the two posts 38 may open laterally with respect to each other. This opening is done in the direction perpendicular to the tensile direction and perpendicular to the various bearing surfaces of the blade root. This degree of freedom allows for a better reproduction of the holding conditions of the blade in operation.

Advantageously, opening of the two portions of the holding system is limited by resilient return means. Such resilient return means are composed of four metallic bars 40 deforming during tensile cycles while staying in their range of elastic deformation. Such bars 40 connect the posts 38 in a direction perpendicular to the tensile axis. They are threaded at their free ends, so as to be fastened by bolting.

In order to check proper operation of the tensile cycles to which the blade roots will be subjected, the machine further comprises means 18 for measuring the opening of the test piece halves during testing. This measurement allows to ensure proper operation and correct positioning of the various parts during testing.

Figure 3:
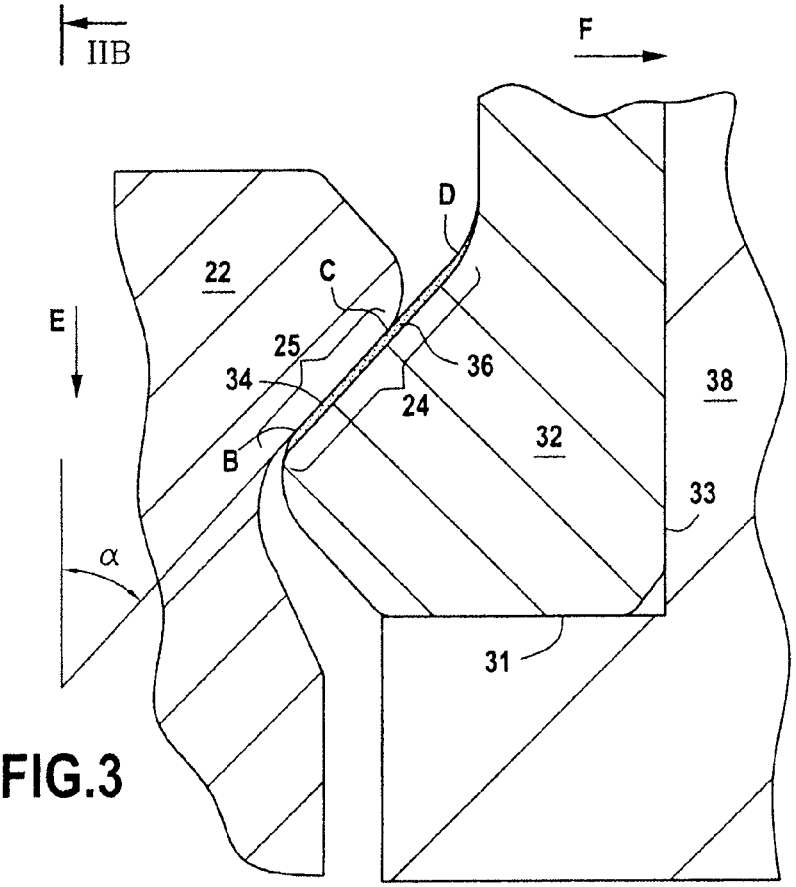
FIG. 3 is an axial sectional view of the bearing surface area of the counter test piece and the test piece halves of the test device.

With reference to FIG. 3, we are going to describe the relative shapes of the counter test piece 32 and the test piece half 32. The test piece half 32 is shown resting on post 38. The test piece half 32 comprises a bearing surface 24 extending between point B and point D. The counter test piece also comprises a bearing surface 25 facing the bearing surface 24 of the test piece half 32. The bearing surface 24 of the test piece half is coated with a coating of the same kind and applied according to the same method as the corresponding area of the blade root. In the relative position of the test piece half 32 and the counter test piece 22, contact is made only in the contact area belonging to the bearing surface 24 of the test piece half, between points B and C. Of course, during tensile testing, the position of this contact area will vary with respect to the bearing surface.

As can be seen in FIG. 3, the bearing surfaces of test piece 22 and test piece half 32 are arranged in a direction sloping or inclined with respect to direction E, which is the tensile direction. This is the inclination to be found where the blade root is fastened to the rotor disk. The angle of inclination $\alpha$ is close to 45°.

The invention claimed is:

1. A device for testing a coating capable of coating a turbomachine rotor blade root, the device comprising:
   two test piece halves, each including a bearing surface coated with the coating;
   one counter test piece including two bearing surfaces; and
   a test machine comprising a first holding system that holds the counter test piece along a tensile axis, a second holding system that holds the test piece halves around the counter test piece, and tensile means for subjecting the holding systems to predetermined tensile cycles along the tensile axis, during which tensile strain is transmitted from one holding system to the other via the respective bearing surfaces contacting each other of the counter test piece and the test piece halves, and wherein the second holding system comprises resilient return means allowing for the two test piece halves to open up in a direction perpendicular to the tensile direction in response to an opening force applied to these two test piece halves by the counter test piece during a tensile cycle.

2. The test device according to claim 1, wherein the side of the test piece halves located on the side of the counter test piece has no undercut.

3. The test device according to claim 1, wherein the bearing surfaces of the test piece halves are sloping with respect to the tensile axis, so as to represent a shape of the bearing surfaces of the turbomachine rotor blade root.

4. The test device according to claim 1, wherein the bearing surfaces of the counter test piece are sloping with respect to the tensile axis, so as to represent a shape of the bearing surfaces of a turbomachine rotor disk tenon.

5. The test device according to claim 1, wherein the resilient return means comprises at least one bar of resilient material, deforming while remaining in its range of elastic deformation during tensile cycles.

6. The test device according to claim 1, wherein the second holding system further comprises two posts parallel to the tensile axis and used for holding the two test piece halves, and a bar connecting the posts according to a direction perpendicular to the tensile axis.

7. The test device according to claim 1, further comprising means for measuring opening of the test piece halves during testing.

8. The test device according to claim 1, wherein the test piece halves include, close to the bearing surfaces thereof, a shape representing turbomachine rotor blade root halves, and the tensile axis is arranged substantially in the radial direction of the blade root halves.

9. The test device according to claim 1, wherein the counter test piece includes, close to the bearing surfaces thereof, a shape representing a shape of a tenon of a turbomachine rotor disk.

10. The test device according to claim 1, wherein the counter test piece is formed of a titanium or nickel base alloy.

11. The test device according to claim 1, wherein the test piece halves are formed of a titanium or nickel base alloy.

* * * * *